United States Patent [19]

Reinicke

[11] Patent Number: 4,486,190

[45] Date of Patent: Dec. 4, 1984

[54] PRECISION MEDICATION DISPENSING SYSTEM AND METHOD

[75] Inventor: Robert H. Reinicke, Mission Viejo, Calif.

[73] Assignee: Consolidated Controls Corporation, El Segundo, Calif.

[21] Appl. No.: 453,594

[22] Filed: Dec. 27, 1982

[51] Int. Cl.³ .............................................. A61M 37/00
[52] U.S. Cl. ...................................... 604/67; 604/891
[58] Field of Search ...................................... 604/65-67, 604/118, 891, 151-153; 3/1.7; 128/DIG. 13

[56] References Cited

U.S. PATENT DOCUMENTS

| | | | |
|---|---|---|---|
| 4,077,405 | 3/1978 | Haerten et al. | 128/214 F |
| 4,146,029 | 3/1979 | Ellinwood | 604/891 |
| 4,231,354 | 11/1980 | Kurtz et al. | 3/1.7 |
| 4,294,248 | 10/1981 | de Figueiredo | 604/65 X |
| 4,360,019 | 11/1982 | Portner et al. | 604/891 |
| 4,373,527 | 2/1983 | Fischell | 128/260 |
| 4,391,598 | 7/1983 | Thompson | 604/65 |
| 4,395,259 | 7/1983 | Preskele et al. | 604/67 |

Primary Examiner—Edward M. Coven
Attorney, Agent, or Firm—Mason, Kolehmainen, Rathburn & Wyss

[57] ABSTRACT

The implantable device includes a medication reservoir, a pulsatile pump and an absolute pressure transducer. The pumping pressure wave developed in the pumping chamber is measured by the absolute pressure transducer whose output is used to adjust the pulsing rate of the solenoid operated pump so that the programmed time averaged rate of infusion of medication into the body is precisely maintained throughout all operating temperature and pressure conditions.

27 Claims, 4 Drawing Figures

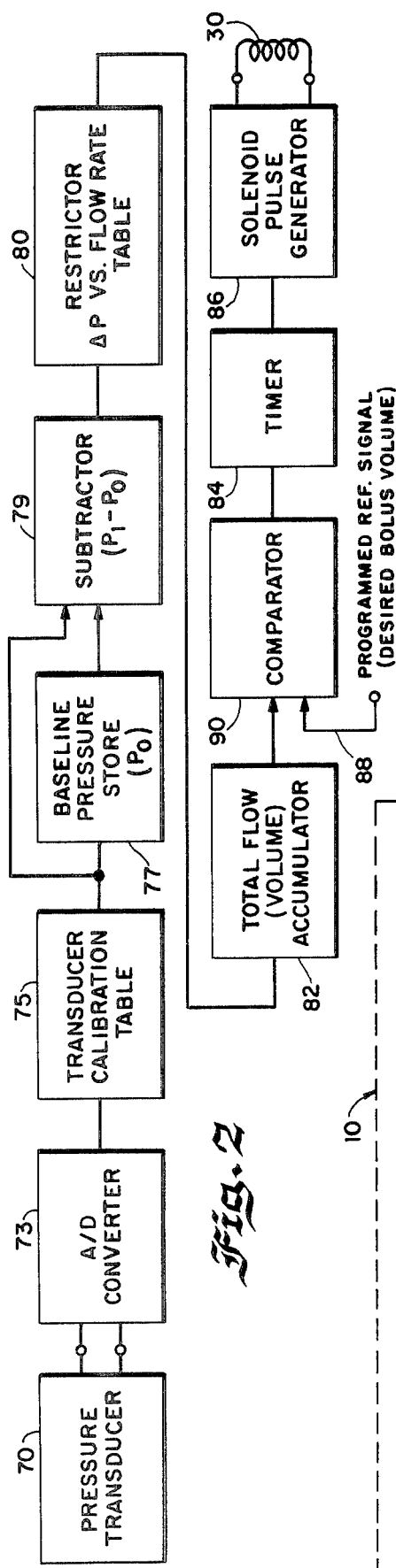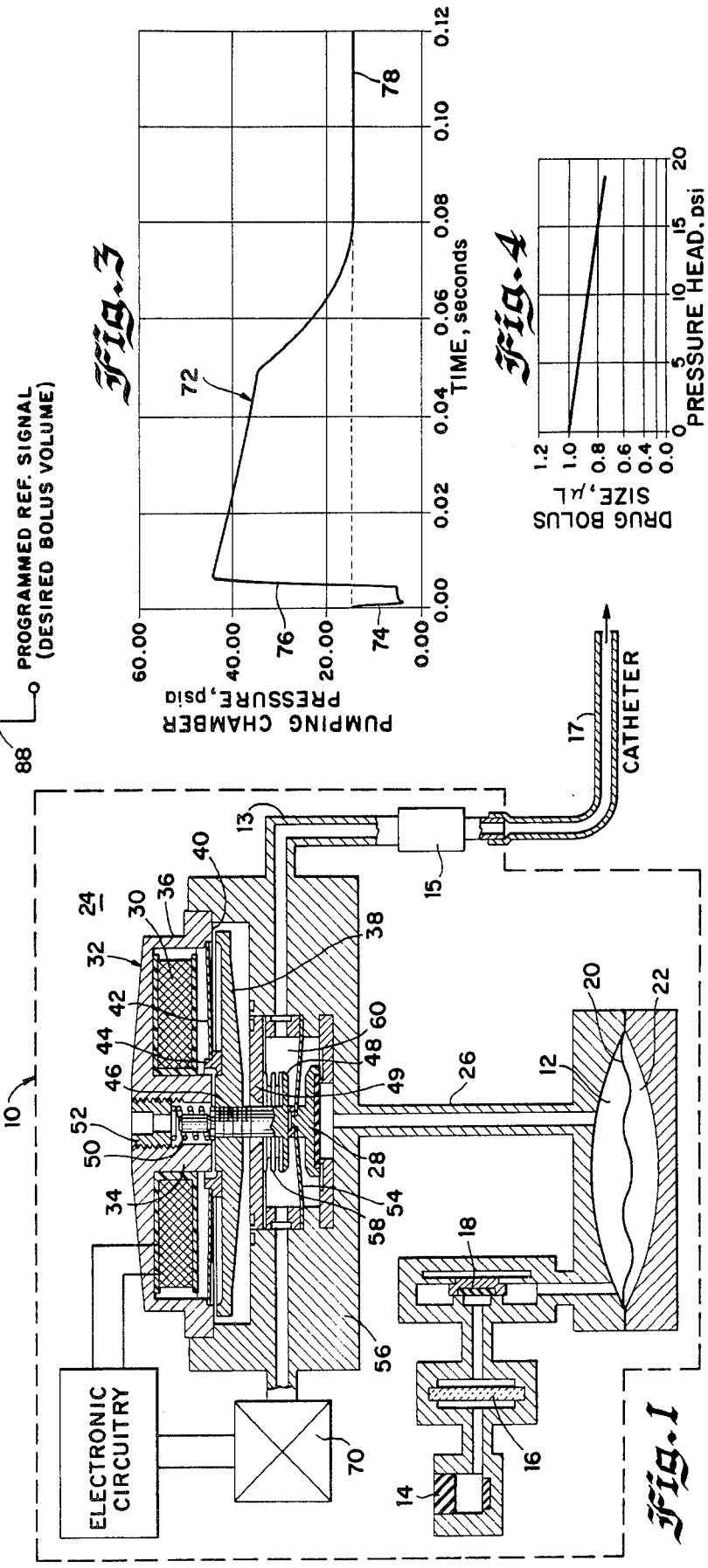

PRECISION MEDICATION DISPENSING SYSTEM AND METHOD

The present invention relates to implantable medication infusion systems and methods, and, more particularly, to so-called pulsatile systems and methods in which medication is dispensed to the body during short dispensing periods separated by relatively long intervals between such dispensing periods.

Many implantable devices in the prior art have employed so-called pulsatile medication dispensing system. Examples of such pulsatile dispensing systems are shown in Summers U.S. Pat. No. 3,527,220; Ellinwood U.S. Pat. No. 3,692,027, Ellinwood U.S. Pat. No. 3,923,060, Thomas et al U.S. Pat. No. 3,963,380; Haerten et al U.S. Pat. No. 4,077,405; Ellinwood U.S. Pat. No. 4,146,029, Moody et al U.S. Pat. No. 4,152,098; Franetzki et al U.S. Pat. No. 4,191,181; Portner U.S. Pat. No. 4,265,241; and Dorman International Publication No. WO 81/00209.

Some of these pulsatile systems have used inlet and outlet check valves in connection with a pumping chamber, the pump element acting to withdraw a metered amount of medication from a reservoir during the intake stroke of the pump and dispensing this metered amount of medication to an outlet catheter during the return stroke of the pump element. In such arrangements, the outlet check valve closes and the inlet check valve opens on the intake stroke of the pump so that medication can be drawn from the reservoir into the pumping chamber.

In other pulsatile systems, an outlet flow restriction device has been employed instead of an outlet check valve, for example, in Haerten et al U.S. Pat. No. 4,077,405. In such devices compliance of the pumping chamber prevents the accurate dispensing of a fixed amount of medication for each stroke of the pump, because the pressure head across the pump will vary with different operating conditions. Variations in the pressure head across the pump will produce corresponding variations in the bolus volume of medication forced through the restrictor during the medication dispensing periods. Such variations in pressure head can occur due to changes in altitude and temperature of the person carrying the implanted device, since the pressure within the body, i.e. the pressure at the outlet of the flow restrictor, varies with changes in altitude, and the pressure at the pump inlet varies with changes in temperature of the medication reservoir.

It is an object of the present invention to provide a new and improved pulsatile medication infusion system and method whereby an outlet flow restrictor may be used and the time averaged rate of infusion of medication into the body may be very accurately controlled under all operating conditions.

It is another object of the present invention to provide a new and improved pulsatile medication infusion system in which the exact amount of medication dispensed during each dispensing period is measured and compared with a reference value, the output of such comparator being employed to vary the timing between dispensing periods so that the overall time averaged rate of infusion corresponds to said reference value.

It is a further object of the present invention to provide a new and improved pulsatile medication dispensing system wherein the accurate measurement of the amount of medication dispensed through a flow restriction device during each medication dispensing period is obtained by measuring the change in pressure in the pumping chamber during the medication dispensing period, converting said pressure measurement into a corresponding flow through said flow restrictor, and integrating said value representing flow to obtain a measurement of the total volume of medication dispensed during the dispensing period.

It is another object of the present invention to provide an integrated inlet check valve and solenoid pump arrangement wherein the loading on the inlet check valve has a substantial value between medication dispensing periods, but this loading force is removed at the beginning of the pumping period so that it does not interfere with the operation of the inlet check valve during the intake stroke of the pump.

It is a further object of the present invention to provide a new and improved integral check valve and solenoid pump arrangement wherein the increased loading on the inlet check valve is obtained by employing the inlet check valve as a stop for the spring biased armature of a solenoid operated pump.

Briefly considered, the present invention provides an implantable device which includes a medication reservoir, a solenoid pump arrangement, and an outlet flow restrictor connected between the pumping chamber and the catheter which infuses medication into the body. An absolute pressure transducer is included in the implantable device and is connected to the pumping chamber so that its electrical output measures the instantaneous pumping pressure transient which is produced within the pumping chamber during medication dispensing periods. Since the pressure at the inlet of the flow restrictor falls to catheter outlet pressure in the intervals between medication dispensing periods, this pressure transducer also measures the internal body pressure at the catheter outlet during such intervals. The output of the pressure transducer is then employed to provide both a measurement of the body pressure during intervals between medication dispensing periods and the variation in pressure within the chamber during a medication dispensing period.

By subtracting the body pressure, or base line pressure, which is obtained during the intervals between medication dispensing periods from the amplitudes of the pumping pressure transient at various points along this transient during a medication dispensing period, a series of differential pressure measurements are developed which represent the differential pressure across the flow restrictor and catheter at various points during the medication dispensing period. These differential pressure signals are then converted to a corresponding flow through the flow restrictor and the individual samples are accumulated, or integrated to provide an output signal accurately representing the total volume supplied to the catheter outlet during each medication dispensing period.

A reference signal is developed corresponding to a desired volume of medication to be dispensed during each dispensing period and the precisely measured volume which is obtained by means of the above-described pressure transducer is then compared with this reference signal to provide an error signal. The error signal is then used to control the time period between successive medication dispensing periods so that the average rate of infusion of medication dispensing periods is maintained at the value called for by the reference signal.

A common problem with the usage of pressure transducers in long life installations is drift of the transducer zero set point. It is of special concern in implantable devices because it is not possible to periodically recalibrate the pressure transducer. An important advantage of the subject invention is that it automatically provides compensation for any transducer drift that might occur, since the same transducer is used to measure the baseline (body) pressure and the pump pressure transient. Since the electronics substract the baseline pressure from the transient pressure, an output drift common to both of these outputs is nulled-out. Typically, output drift applies throughout the entire output range of a pressure transducer, so the present invention provides a very effective means to eliminate the effect of output drift of the absolute pressure transducer.

In accordance with a further aspect of the invention the solenoid pump includes a bipole solenoid coil which is included in a magnetic circuit including a movable armature which is spring biased against an inlet check valve which is provided between the medication reservoir and the pumping chamber. The biased armature thus provides a substantial loading force on the inlet check valve during periods between medication dispensing periods so as to prevent leakage from the body into the pumping chamber and hence into the reservoir. However, soon after the solenoid coil is energized the armature is lifted off of the inlet check valve and removes its loading force so that the inlet check valve can open to permit withdrawal of a predetermined small amount of medication from the reservoir into the pumping chamber.

The invention both as to its organization and method of operation, together with further objects and advantages thereof, will best be understood by reference to the following specification taken in connection with the accompanying drawings in which:

FIG. 1 is a block diagram of an implantable medication infusion system embodying the features of the present invention;

FIG. 2 is a block diagram of a portion of the electronic circuitry of the implantable device of FIG. 1;

FIG. 3 is a graph of the pumping chamber pressure transient which is produced in the system of FIG. 1; and FIG. 4 is a graph of the drug bolus size which is produced at different pressure heads across the pump (from the medication reservoir to the outlet of the catheter) due to the intrinsic compliance of the pump.

Referring now to FIG. 1, the implantable device 10 of the present invention is therein illustrated as comprising a medication reservoir 12 which can be refilled while the device 10 remains implanted by inserting a hypodermic needle into an entry septum 14 and supplying medication through a fill filter 16 and a fill check valve indicated generally at 18. A diaphragm 20 is provided as one wall of the reservoir 12 and the chamber 22 behind the diaphragm 20 is filled with a fluid which is in a two-phase (gas and liquid) state at body temperature to maintain a reference pressure within the reservoir 12 which is slightly less than a chosen minimum body pressure, i.e. the body pressure which may occur when the patient who carries the implanted device 10 is at a designated maximum altitude.

The reservoir 12 communicates with an integral inlet check valve and solenoid pump arrangement indicated generally at 24 through the conduit 26. The outlet of the integral unit 24 is connected through a conduit 13 to a flow restriction device indicated generally at 15, the output of flow restriction device 15 being connected to a catheter 17 which is employed to dispense medication into a desired portion of the body in which the implantable device 10 is implanted.

An inlet check valve 28 is mounted so as normally to close the conduit 26. A solenoid coil 30 which is mounted in a magnetic structure or housing 32 which includes a central core portion 34 and an annular outer wall portion 36, is arranged to attract a movable armature 38 when the coil 30 is energized so as to lift the armature 38 upwardly into engagement with the bottom surface 40 of the outer rim portion 36 of the housing 32. The armature is mounted within the housing 32 for limited vertical movement by means of the Belleville washer 42 which is positioned between the inner wall 36 and an annular flange portion 44 provided near the center of the armature 38. A central stud 46 which is threaded into the center of the armature 38 and extends downwardly therefrom is provided with a transversely extending head portion 48 which normally rests on the top surface of the inlet check valve 28 and is connected to a bellows 58 which extends between the head portion 48 and a plate 49 so that the portion 48 forms a movable wall portion of a pumping chamber 60.

A coil spring 50 is positioned between a member 52, which is threaded into the housing 32, and the upper surface of the armature 38 so as to provide an additional biasing force which urges the armature downwardly so that the head portion 48 is biased into engagement with the inlet check valve 28 and provides an initial loading force of substantial value for this inlet check valve.

A flexible member 54 which may be in the form of a multi-fingered spider, is connected between the main housing 56 of the implantable device and the central portion of the inlet check valve 28 so as to maintain this check valve in registration with the conduit 26 during opening and closing thereof.

When the solenoid coil 30 is energized it lifts the armature 38 upwardly and removes the loading force thereof from the inlet check valve 28. At the same time the head portion 48 is moved upwardly and the bellows 58 compressed so that the volume of the pumping chamber 60 is increased. As soon as the head portion 48 is lifted off of the upper end of the check valve 128, this inlet check valve remains biased to its closed position only by the relatively small biasing force provided by the mounting member 54 thereof and as soon as the differential pressure across this check valve increases slightly and exceeds the cracking pressure of this valve, the inlet valve 28 opens and admits medication into the pumping chamber 60. This increase is differential pressure across the inlet valve 28 occurs as soon as the solenoid 30 is energized and the head portion 48 and bellows 58 start to move upwardly. Accordingly, the inlet valve effectively moves upwardly with the bellows 58 when the solenoid coil 30 is energized.

When the coil 30 is energized the upward movement of the armature 38 is very fast and fluid cannot immediately enter the pumping chamber until the inlet valve 28 is opened. Accordingly, it is necessary that the effective diameter of the inlet valve 28 be at least as great as and preferably greater than the effective diameter of the bellows so that as the inlet valve 28 moves upwardly it displaces a volume at least equal to the increase in volume produced by upward movement of the bellows. For example, if the effective diameter of the bellows 58, i.e. the diameter half way between the inner and outer diameters of the convolutions of the bellows, is 0.160 inches the effective diameter of the inlet valve 28 is preferably in the order of 0.20 inches.

If the effective diameter of the inlet valve 28 is smaller than the effective diameter of the bellows 58, the pressure within the pumping chamber 60 will become so greatly reduced during the initial portion of the intake stroke that vaporization and cavitation within the pumping chamber will occur. For example, if we assume that the bellows 58 has an effective diameter of 0.16 inches and is moved upwardly 0.003 inches when the coil 30 is energized and the effective diameter of the inlet valve 28 is assumed to be one half that of the bellows 58, i.e. 0.08 inches, the area of the inlet valve 28 will be ¼ that of the bellows 58 and the inlet valve 28 would have to move up a distance of 0.012 inches to displace an amount of fluid equal to the increase in volume due to compression of the bellows. However, upward movement of the inlet valve 28 is limited by the head portion 48 to 0.003 inches so that the pressure within the chamber 60 will be drastically reduced and cause vaporization of the fluid and improper operation of the pump.

The inlet check valve 28 returns to its initial closed position after a volume of medication equal to that of the compression of the bellows 58 (typically one microliter) flows into the pumping chamber 60 and increases the pumping chamber pressure to reduce the pressure differential across the inlet check valve 28 to its reseat value.

It should be noted that the motions of the small solenoid operated bellows 58 and the inlet check valve 28 during the intake stroke of the solenoid actuated pump, are quite fast. For example, the upward motion of the bellows 58 when the coil 30 is energized will take typically on the order of 0.001 seconds. The inlet check valve 28 will follow this upward movement of the bellows 58 and then takes a substantially longer time, in the order of 0.005 seconds to settle back onto its seat as fluid flows into the chamber 60 and increases the pumping chamber pressure.

The outlet restrictor 15 which is connected to the outlet of the pumping chamber, is quite small and may be equivalent to a 0.001 inch diameter thin plate orifice, as will be described in detail hereinafter. Accordingly, such a flow restriction device allows only negligible backflow into the pumping chamber 60 during the extremely fast intake stroke of the pump.

Following closure of the inlet check valve 28, the solenoid coil is de-energized and the mechanical spring forces of the deflected Belleville washer 42, the spring 50, and the compressed bellows 58, acting on the effective area of the head portion 48, increase the pumping chamber pressure above the body pressure at the catheter outlet. This forces medication from the pumping chamber 60 through the outlet restrictor 15 and out the catheter 17. This exhaust stroke occurs very slowly relative to the previous intake stroke and its rate is determined by the pumping chamber pressure level, the outlet restrictor size and the body pressure at the catheter outlet.

After the solenoid bellows 58 extends and the solenoid armature reaches its de-energized position on top of the inlet check valve 28, the pumping chamber pressure equalizes to the catheter outlet (body) pressure and infusion of medication ceases.

Flow restriction device 15 which is provided at the pumping chamber outlet, has substantial resistance to the flow of medication in its reverse direction, and can also have substantial restriction in its forward direction. Accordingly, the flow restriction device 15 prevents backflow of any significance during the solenoid bellows intake stroke. Although the restrictor 15 can be a conventional orifice, such as a thin plate orifice, it preferably comprises another type of fluid restrictor, such as a series of chemically milled plates of irregular shape which provide a long tortuous flow passage which provides a high pressure drop while having a relatively large flow area. Such a device has a flow passage size which is larger than that of a thin plate orifice and hence will not as readily plug with contamination in the medication. In the alternative, a length of capillary tubing may act as the restrictor 15. In this connection it will be understood that in some instances the catheter itself may act as an additional outlet restrictor depending upon the internal diameter and length of the catheter.

After the exhaust stroke has been completed and medication has been forced out of the catheter 17 a medication dispensing period is completed. Subsequent medication dispensing periods are repeated, by successive energizations of the solenoid coil 30, so as to provide a desired average flow rate of medication out of the catheter 17. However, it will be understood that with normal rates of flow of medication, the intervals between medication dispensing periods are quite long as compared to the medication dispensing periods themselves. For example, the medication dispensing period may last for 0.08 seconds, whereas the time interval to the next medication dispensing period may be six seconds or longer.

With such a long time period between medication dispensing periods, the flow restrictor 15 permits the pressure at the inlet conduit 14 of the flow restrictor 15 to fall to body pressure. Accordingly, when the patient who carries the implanted device changes altitude, as for example when he goes from sea level to ten thousand feet altitude, his body pressure changes substantially with the result that the operating conditions of the medication dispensing pump 24 are changed substantially. In the case of sea level operation the base line pressure, i.e. the pressure between medication dispensing periods will be substantially higher than it is when the patient is at ten thousand feet altitude causing the pressure head across the pump to increase.

As indicated in FIG. 4, when the pressure head across the pump increases the volumetric efficiency of the pump decreases due to the compliance of the components of the pump, particularly the elastomer valve seat of the inlet valve 28 and the bellows 48, so that the pump will infuse a smaller sized bolus of medication during the medication dispensing period. Also, the temperature of the reservoir 12 will affect the inlet pressure to the pump and hence the volumetric efficiency thereof so that the bolus size will change. For example, the pressure at the outlet of the reservoir 12 may change from 7 to 10 psi with a variation in body temperature of from 94° F. to 104° F. Accordingly, if a patient carrying the implanted device 10 is at 10,000 feet altitude and has a body temperature of 104° F. the pressure head across the pump is 10 psia. on the inlet and 10.1 psia. on the outlet, i.e. a pressure head of 0.1 psi., which accordingly to FIG. 4 would produce a bolus size of 1.0 microliter. On the other hand, if the patient is at sea level and his body temperature is 94° F. the pressure head across the pump would be 7.0 psia. at the inlet and 14.7 psia. at the outlet, i.e. a pressure head of 7.7 psi. which according FIG. 4 would produce a bolus size of approximately 0.9 microliters each medication dispensing period. While the above examples are worst-case conditions, it is nevertheless evident that a fixed timing rate of six seconds will not result in a desired average rate of flow of medication into the body under different operating conditions which affect the volumetric efficiency of the pump due to the compliance of various components thereof. In addition, variations in manufacturing tolerances of the extremely small components of the integral inlet check valve and solenoid pump 24 can cause variations in the actual volume of medication dispensed during each medication dispensing period. Also, life and wear caused variations may also introduce further changes in the volume of medication dispensed each time the solenoid coil 30 is energized.

In accordance with an important aspect of the present invention, the pressure within the pumping chamber 60 is measured by means of an absolute pressure transducer 70, and the output of this pressure transducer is employed to control the timing of solenoid coil actuations so as to maintain a programmed, time averaged rate of flow of medication into the body. More particularly, the pressure transducer 70 provides an output signal which is proportional to the instantaneous pressure existing in the pumping chamber 60 during the entire medication dispensing period. This pumping pressure transient 72, which is shown in FIG. 3, includes an initial negative going portion 74 corresponding to the decrease in pressure within the chamber 60 during the solenoid bellows intake stroke and a positive portion 76 of much longer duration during which time the pressure in the pumping chamber 60 gradually decreases from an initial high value during the time when medication is forced through the flow restriction device 15 and the catheter 17 into the body. The pressure in the pumping chamber 60 then falls to a base line value 78 which is equal to body pressure, due to the equalization of pressure through the flow restriction device 15, and remains at this base line value for approximately six seconds or longer until the next medication period. If, for example, the patient is at sea level, the base line pressure 78 will be 14.7 psia., as shown in FIG. 3.

It will thus be seen that the pumping pressure transient 72 lasts for only a brief interval of approximately 0.08 seconds, while the time interval between medication dispensing periods is in the order of six seconds or longer. Since the base line pressure 78 corresponds to the body pressure at the outlet of the flow restriction device 15 during the medication dispensing period, this base line pressure may be subtracted from the instantaneous value of the pressure pumping transient 72 so as to provide an accurate measure of the differential pressure across the flow restriction device 15 and catheter 17 during the medication dispensing period. Then, the differential pressure vs. flow rate characteristic of the flow restricting device 15 and catheter 17 can be employed to provide an accurate measure of the actual flow of medication through the flow restriction device 15 and catheter 17 at various times during the pumping transient 72. By integrating these instantaneous flow rates, an output signal may be developed which is accurately proportional to the total volume of medication actually dispensed during a medication dispensing period. Furthermore, this output signal will reflect all changes in mechanical and operating condition variables which influence the volume of medication dispensed. Accordingly, this output signal may be compared to a programmed reference signal, which represents a desired volume of medication to be dispensed at the catheter outlet during each dispensing period at a nominal rate of occurrence of said dispensing periods, and the resultant error signal may be employed to vary the timing of coil actuations from this nominal rate so that a desired time averaged rate of infusion into the body is maintained despite changes in any or all of these variables.

As stated above, this variation or "trimming" of the interval between pumping periods, is necessary to achieve accurate medication infusion dosage in accordance with programmed requirements throughout the range of operating pressures and temperatures of an implanted system which determine the pump pressure head and efficiency of the pump, as shown in FIG. 4. This range of operating conditions includes reservoir pressure variations due to temperature changes that in turn change the vapor pressure of the material in the chamber 22. Also, changes in the reservoir diaphragm pressure as medication is displaced from the reservoir 12 may influence the volume of medication dispensed. Body pressure relative to ambient variations, as well as ambient pressure variations primarily due to altitude changes, may also affect the volume of medication dispensed.

Referring now to FIG. 2, a portion of the electronic circuitry included in the implanted device 10 is shown in this figure, whereby the output of the pressure transducer may be employed to control the time periods between actuations of the solenoid coil 30 so as to provide a desired time averaged rate of infusion of medication into the body. More particularly, the output of the pressure transducer 70 is supplied to an analog to digital converter 73 which converts the analog electrical output of the pressure transducer 70 into a corresponding digital signal. Since the output of the pressure transducer 70 may be somewhat non-linear, it is desirable to correct the output of this transducer so that an extremely accurate measurement of the volume of medication dispensed during a particular medication dispensing period is obtained. To this end, the output of the analog-to-digital converter 73 is connected to a transducer calibration lookup table 75 which provides a correction which is unique to the particular pressure transducer 70 which is used in the implanted device 10. More particularly, the output of the transducer calibration lookup table 75 provides a corrected digital output which is linear with respect to pressure.

As discussed generally heretofore, the output of the pressure transducer 70 measures body pressure during the intervals between medication dispensing periods, i.e. during the base line portion 78 of the pressure transducer output shown in FIG. 3. This is because the flow restriction device 15, unlike an outlet check valve, permits the inlet pressure in the conduit 13, and hence the pressure in the pumping chamber 60 measured by the pressure transducer 70, to fall to body pressure during the relatively long intervals between medication dispensing periods.

The base line pressure 78, which is equal to body pressure, is sampled and stored in a sample and hold circuit 77 which is controlled to sample the output of the pressure transducer 70 at some convenient point during the interval between medication dispensing periods, preferably immediately before or immediately after a dispensing period.

The body pressure ($P_o$) which is stored in the sample and hold circuit 77 is then subtracted from the pumping pressure transient ($P_1$) in a subtractor 79. The subtractor 79 samples the pumping pressure transient 72 at a sufficiently high rate that a number of samples of the differential pressure across the flow restriction device 15 is obtained during both the negative portion 74 of the pumping pressure transient and the positive portion 76 thereof. Preferably, the pumping pressure transient 72 is sampled at the approximate rate of 1000 samples per second. By storing the base line pressure ($P_o$) and subtracting it from the pumping pressure transient 72, a large number of samples is obtained representing the actual differential pressure across the flow restrictor 15 at successive times during a medication dispensing period.

The output of the subtractor 79 is then supplied to a restrictor differential pressure versus flow rate lookup table 80. This lookup table provides an output signal proportional to the flow rate through the flow restrictor 15 (and catheter 17 if necessary) for each particular value of differential pressure across this flow restrictor. Accordingly, for each sample of differential pressure developed by the subtractor 79, a corresponding output is developed at the output of the lookup table 80 which converts this differential pressure into a corresponding flow rate through the flow restrictor 15. The resulting flow rates, which are both negative during the negative portion 74 of the pumping transient, and are positive during the positive pumping portion 76 thereof, are summed in a total flow accumulator 82 so as to provide an output signal which is proportional to the actual volume of medication which flows through the flow restrictor 15 during a particular medication dispensing period.

In order to establish a nominal rate of occurrence of dispensing periods, i.e. actuations of the solenoid coil 30, a timer 84 is provided which controls a solenoid pulse generator 86 which in turn supplies a pulse of current to the solenoid coil 30 of the appropriate duration to attract the armature 38 and introduce the desired amount of medication into the pumping chamber 60. As discussed generally heretofore, this timer may control the generator 86 to produce medication dispensing periods at the nominal rate of one every six seconds, for example. Under these nominal conditions the integral valve and pump 24 may produce, for example, one microliter of medication which is dispensed to the body every six seconds. However, it will be understood that any desired time averaged rate of infusion of medication into the body may be established by any suitable programmable arrangement. For example, the rate of infusion of medication into the body may be programmed to substantially increase during mealtimes, in the case of the infusion of insulin into the body.

The electronic circuitry for establishing a desired rate of infusion may be of any suitable type such as a microprocessor, which is included within the implanted device 10 and provides a programmed reference signal which is supplied to the input terminal 88 connected to one input of a comparator 90. The other input of the comparator 90 is connected to the output of the accumulator 82 which represents the actual volume of medication dispensed during a particular medication dispensing periods.

The reference signal 88 represents a desired volume of medication to be dispensed to the catheter outlet at a nominal rate of occurrence of say, six seconds. If the actual volume of medication dispensed does not equal the programmed reference value on the input terminal 88, an error signal is developed in the output of the comparator 90 which is supplied to the timer 84 and is employed to vary the rate of occurrence of pulses developed by the timer in the correct direction to hold the time averaged rate of infusion of medication into the body at the desired value.

For example, if the total volume signal developed by the accumulator 82 is larger than the reference signal on the input terminal 88, thus indicating that a larger than desired volume of medication has been dispensed during that particular medication dispensing period, the frequency of the timer 84 is decreased so that a longer time interval ensues before the next medication dispensing period. Accordingly, the average rate of infusion of medication when measured over at a number of medication dispensing periods is thus automatically adjusted so that the rate of infusion is equal to the desired value represented by the reference signal on the input terminal 78.

On the other hand, if the actual volume measured by the accumulator 82 is less than the desired amount, the output of the comparator 90 will increase the frequency of the timer 84 so that a shorter time interval elapses before the next medication dispensing period. Accordingly, the time averaged rate of infusion of medication, when measured over a number of medication periods, will be brought back to the desired value represented by the signal on the terminal 88. It will thus be seen that with the apparatus of the present invention, a precise time averaged rate of infusion of medication into the body can be provided under programmed control and taking into account all of the mechanical and operating condition variables which tend to influence the volume of medication dispensed by the pumping unit 24.

While the arrangement of the present invention has been illustrated in FIG. 2 as operating on a digital basis, which is most suitable for microprocessor applications, it will also be understood that the output of the pressure transducer can be employed on an analog basis to provide the abovedescribed feedback compensation for variations in the total flow of medication during each medication dispensing period. More particularly, it is only necessary to store the analog value of the output of the pressure transducer 70 during the base line portion 78 and then compare this stored value with the analog value of the pumping pressure transient 72 at a relatively high sampling rate during this pumping pressure transient and then subtract the stored base line value therefrom. The resultant differential pressure signal may then be converted into a corresponding flow rate signal corresponding to the actual flow through the flow restrictor 15 at that differential pressure and the output thereof integrated to provide an output signal proportional to the total volume of medication flowing through the restrictor 15 during that particular medication dispensing period, as will be readily understood by those skilled in the art.

While there have been illustrated and described various embodiments of the present invention, it will be apparent that various changes and modifications thereof will occur to those skilled in the art. It is intended in the appended claims to cover all such changes and modifications as fall within the true spirit and scope of the present invention.

What is claimed as new and desired to be secured by Letters Patent of the United States is:

1. In a system for infusing medication into a body, the combination of, a medication reservoir, a flow restriction means having an outlet for infusing medication into the body, metering means connected betwen said reservoir and the inlet of said flow restriction means for periodically supplying a small portion of the medication in said reservoir to the inlet of said flow restriction means during successive spaced apart dispensing periods, means for measuring the exact amount of medication supplied to said flow restriction outlet during each dispensing period, said measuring means including a pressure transducer for developing a signal corresponding to the pressure transient developed at said inlet of said flow restriction means during each of said dispensing periods, and means responsive to said measuring means for varying the time between successive dispensing periods so as to maintain the rate of infusion of medication into the body at a desired value.

2. The combination of claim 1, wherein said flow restriction means allows the pressure at the inlet thereof to become equal to the pressure at said outlet in the intervals between dispensing periods, and means for periodically sampling the output of said pressure transducer during one of said dispensing periods and subtracting from each sample the output of said pressure transducer during said intervals to obtain successive samples representing the differential pressure across said flow restriction means during said one dispensing period.

3. The combination of claim 2, wherein the output of said pressure transducer is subject to drift and said differential pressure samples are compensated for such drift by subtracting the output of the pressure transducer during the interval between dispensing periods from the output of the pressure transducer during one of the dispensing periods.

4. The combination of claim 2, which includes means for converting said differential pressure samples into signals representing the corresponding flow of medication through said flow restriction means, and means responsive to said signals for developing an output signal representing the total volume of medication supplied to said outlet during each of said dispensing periods.

5. In a system for infusing medication into a body, the combination of, a medication reservoir, a medication outlet for infusing medication into the body, positive displacement pump means connected between said reservoir and said outlet and including a pumping chamber and a pump element movable through a predetermined stroke within said chamber to force medication from said reservoir into said medication outlet, a flow restrictor positoned between said pumping chamber and said outlet, said flow restrictor allowing the pressure within said pumping chamber to become equal to the pressure at said outlet in the intervals between strokes of said pump element, and a pressure transducer for measuring the absolute pressure within said pumping chamber and developing an electrical signal which varies in accordance with the instantaneous pressure within said pumping chamber, whereby said electrical signal includes a base line portion proportional to the pressure at said outlet during said intervals and a pumping pressure transient portion which varies in accordance with variations in the pressure within said chamber during pumping strokes of said pump element, and means controlled by said electrical signal for varying the rate at which said pump is actuated so as to maintain a predetermined average rate of flow of medication to said outlet.

6. The combination of claim 5, which includes means for storing a value proportional to said base line portion of said electrical signal, and means for periodically subtracting said base line value from the instantaneous value of said electrical signal during said pumping pressure transient portion of said electrical signal to obtain successive values of the differential pressure across said flow restrictor during said pumping pressure transient, and means controlled by said successive differential pressure values for calculating the actual flow of medication to said outlet during said pumping pressure transient.

7. The combination of claim 6, which includes means for developing a reference signal corresponding to a desired flow of medication to said outlet, and means jointly responsive to said successive differential pressure values and said reference signal for controlling the rate at which said pump element is actuated so as to maintain the flow of medication to said outlet at said desired value.

8. The combination of claim 7, which includes means for converting said successive differential pressure values into corresponding rates of flow through said restrictor, and means for integrating said successive converted flow rates to obtain an output corresponding to the total volume of medication supplied to said outlet during one stroke of said pump element.

9. In a system for infusing medication into a body, the combination of, a medication reservoir, a medication outlet for infusing medication into the body, positive displacement pump means connected between said reservoir and said outlet and including a pumping chamber and a pump element movable through a predetermined stroke within said chamber to force medication from said reservoir into said medication outlet, a pressure transducer for developing an electrical signal corresponding to the pressure transient developed within said pumping chamber during one stroke of said pump element, means for generating successive signals corresponding to the flow of medication to said outlet during successive portions of said pressure transient, means responsive to said successive signals for developing an output signal corresponding to the total volume of medication supplied to said outlet during said one stroke of said pump element, and means controlled at least in part by said output signal by varying the rate at which said pump element is stroked to maintain the volume of medication supplied to said outlet per unit of time at a predetermined value.

10. The combination of claim 9, which includes means for integrating said successive signals to obtain said output signal.

11. In a system for infusing medication into a body, the combination of, a medication reservoir, a medication outlet for infusing medication into the body, positive displacement pump means connected between said reservoir and said outlet and including a pumping chamber and a pump element movable through a predetermined stroke within said chamber to force medication from said reservoir into said medication outlet, a flow restrictor connected between said pumping chamber and said outlet, said flow restrictor allowing the pressure within said pumping chamber to become equal to the pressure at said outlet in the intervals between strokes of said pump element, means for measuring the precise volume of medication pumped to said outlet on each stroke of said pump element, and means controlled at least in part by said measuring means for varying the rate at which said pump element is stroked to maintain the volume of medication supplied to said outlet per unit of time at a predetermined value.

12. In a system for infusing medication into a body, the combination of, a medication reservoir, a medication outlet for infusing medication into the body, positive displacement pump means connected between said reservoir and said outlet and including a pumping chamber and a pump element movable through a predetermined stroke within said chamber to force medication from said reservoir into said medication outlet, a flow restrictor connected between said pumping chamber and said outlet, said flow restrictor allowing the pressure within said pumping chamber to become equal to the pressure at said outlet in the intervals between strokes of said pump element, a pressure transducer for developing an electrical signal corresponding to the pressure transient developed within said pumping chamber during one stroke of said pump element, means for generating a series of signals corresponding to the differential pressure across said flow restrictor at different points along said pressure transient, means responsive to each of said series of differential pressure signals for developing a signal representing the corresponding flow of medication through said flow restrictor, means responsive to said series of flow signals for developing an output signal representing the total volume of medication supplied to said outlet during said one stroke of said pump element, and means controlled at least in part by said output signal for varying the rate at which said pump element is stroked to maintain the volume of medication supplied to said outlet per unit of time at a predetermined value.

13. The combination of claim 12, wherein said series of flow signals are digital signals, and accumulator means for summing said series of flow signals to provide said output signal.

14. In a system for infusing medication into a body, the combination of, a medication reservoir, a medication outlet for infusing medication into the body, positive displacement pump means connected between said reservoir and said outlet and including a pumping chamber and a pump element movable through a predetermined stroke within said chamber to force medication from said reservoir into said medication outlet, a flow restrictor connected between said pumping chamber and said outlet, said flow restrictor allowing the pressure within said pumping chamber to become equal to the pressure at said outlet in the intervals between strokes of said pump element, a pressure transducer for developing an electrical signal corresponding to the pressure transient developed within said pumping chamber during one stroke of said pump element, means responsive to said electrical signal for generating a differential pressure signal which varies in accordance with the differential pressure across said flow restrictor during said pressure transient, means for converting said different pressure signal into a corresponding flow rate signal whose amplitude varies in accordance with variations in flow through said flow restrictor during said pressure transient, means for integrating said flow rate signal, thereby to provide an output signal representing the total volume of medication supplied to said outlet during said one stroke of said pump element, and means controlled at least in part by said output signal for varying the rate at which said pump element is stroked to maintain the volume of medication supplied to said outlet per unit of time at a predetermined value.

15. The combination of claim 12, which includes means for actuating said pump element at a variable rate, means for generating a reference signal corresponding to a desired flow of medication to said outlet, means for comparing said reference signal with said output signal to develop an error signal corresponding to the difference therebetween, and means controlled by said error signal for varying the rae of actuation of said pump element by said actuating means to maintain said desired flow of medication to said outlet.

16. In a system for infusing medication into a body, the combination of, a medication reservoir, a medication outlet for infusing medication into the body, positive displacement pump means connected between said reservoir and said outlet and including a pumping chamber and a pump element movable through a predetermined stroke within said chamber to force medication from said reservoir into said medication outlet, means for actuating said pump element at a variable rate, means for generating a reference signal corresponding to a desired flow of medication to said outlet, means for developing an output signal representing the precise volume of medication pumped to said outlet on each stroke of said pump element, said means for developing an output signal including a pressure transducer for developing an electrical signal corresponding to the pumping pressure transient developed within said pumping chamber during one stroke of said pump element, means for comparing said reference signal and said output signal to develop an error signal corresponding to the difference therebetween, and means controlled by said error signal for varying the rate of actuation of said pump element by said actuating means to maintain said desired flow of medication to said outlet.

17. The combination of claim 16, which includes pressure transducer calibration means for modifying said electrical signal to correct for non-linearity in the output of said pressure transducer.

18. The combination of claim 16, which includes A/D converter means for developing a digital signal corresponding to the output of said pressure transducer.

19. The combination of claim 18, which includes transducer calibration means connected to the output of said A/D converter means to correct for non-linearity in the output of said pressure transducer.

20. The combination of claim 16, which includes a flow restrictor connected between said pumping chamber and said outlet, said flow restrictor allowing the pressure within said pumping chamber to become equal to the pressure at said outlet in the intervals between strokes of said pump element.

21. The combination of claim 20, which includes means for storing a value corresponding to the pressure in said pumping chamber during said intervals.

22. The combination of claim 21, which includes means for periodically subtracting said stored value from the output of said pressure transducer during said pressure transient to obtain a succession of signals representing the differential pressure across said flow restrictor at different times during said pressure transient.

23. The combination of claim 22, which includes means for converting said succession of signals into signals representing the flow rate through said restrictor corresponding to each of said differential pressure signals.

24. The combination of claim 23, which includes means for combining said flow rate signals to provide said output signal.

25. The combination of claim 21, which includes means for periodically sampling said pressure transient to provide successive values corresponding to the amplitude of said pressure transient relative to said stored value at different times during said pressure transient.

26. The combination of claim 25, which includes means controlled by said successive values for developing said output signal.

27. In a system for infusing medication into a body, the combination of, a medication reservoir, a medication outlet for infusing medication into the body, positive displacement pump means connected between said reservoir and said outlet and including a pumping chamber and a pump element movable through a predetermined stroke within said chamber to force medication from said reservoir into said medication outlet, means for actuating said pump element at a variable rate, means for generating a reference signal corresponding to a desired flow of medication to said outlet, a flow restrictor connected between said pumping chamber and said outlet, said flow restrictor permitting the pressure within said pumping chamber to become equal to the pressure at said outlet in the intervals between strokes of said pump element, means for developing a first signal corresponding to the pressure in said chamber during said intervals, means for developing a second signal which varies in accordance with variations in the pressure within said chamber during strokes of said pump element, means responsive to said first and second signals for developing a control signal means for comparing said reference signal and said control signal to develop an error signal corresponding to the difference therebetween, and means controlled by said error signal for varying the rate of actuation of said pump element by said actuating means to maintain said desired flow of medication to said outlet.

* * * * *